United States Patent [19]

Newland

[11] Patent Number: 5,049,698

[45] Date of Patent: Sep. 17, 1991

[54] PROCESS FOR MANUFACTURING 2-CHLORO-1,3-DIKETO COMPOUNDS

[75] Inventor: Gordon C. Newland, Kingsport, Tenn.

[73] Assignee: Eastman Kodak Company, Rochester, N.Y.

[21] Appl. No.: 855,268

[22] Filed: Apr. 24, 1986

[51] Int. Cl.$^5$ .............................................. C07C 69/66
[52] U.S. Cl. ..................... 560/174; 560/250; 560/253; 558/414; 558/445; 564/199; 564/200
[58] Field of Search ....................... 560/174, 253, 250; 564/199, 200; 558/414, 445

[56] References Cited

U.S. PATENT DOCUMENTS 4,468,356  8/1984  Van Sickle et al. ................. 560/174

FOREIGN PATENT DOCUMENTS 2329817  1/1974  Fed. Rep. of Germany ...... 560/174

Primary Examiner—José G. Dees
Attorney, Agent, or Firm—John F. Stevens; William P. Heath, Jr.

[57] ABSTRACT

A novel process for producing 2-chloro-1,3-diketo compounds of the formula

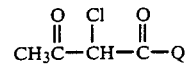

wherein Q is an amino, substituted amino or hydrocarbyloxy group, e.g., —OCH$_3$, wherein the 1,3-diketo precursor in solution in a low boiling alcohol is neulized in a special chlorinator with chlorine or a mixture of nitrogen and chlorine, and wherein the chlorination of the nebulized precursor solution takes place extremely rapidly at relatively high temperatures in a chlorination zone, the product being recovered by condensation on the cooled chlorinator walls and stripping of the alcohol solvent. A representative product is 2-chloro-N,N-dimethylacetoacetamide (2CDMAA), a useful intermediate for the production of insecticides, drugs, dyes and other complex compounds.

9 Claims, No Drawings

PROCESS FOR MANUFACTURING 2-CHLORO-1,3-DIKETO COMPOUNDS

This invention concerns a novel process for synthesizing 2-chloro-1,3-diketo compounds of the formula $$CH_3\overset{O}{\overset{\|}{C}}-\overset{Cl}{\overset{|}{CH}}-\overset{O}{\overset{\|}{C}}-Q$$

wherein Q is an amino, substituted amino or a hydrocarbyloxy group such as alkoxy.

Typical Q groups include amino and the various substituted amino moieties such as methylamino; dimethylamino; diethylamino; N-ethyl-N-cyclohexylamino; N-ethyl-N-benzylamino; and N-methyl-N-phenylamino; and the various hydrocarbyloxy moieties such as methoxy; ethoxy; cyclohexoxy; phenoxy; and benzyloxy.

A representative and preferred product of the present invention is 2-chloro-N,N-dimethylacetoacetamide (2CDMAA), a useful intermediate for the production of insecticides, drugs, dyes and other complex chemicals. Preparations of 2CDMAA by the usual procedures, for example, by the use of sulfuryl chloride for chlorinating 1,3-diketones are typically complicated by the production of the 2,2-dichloro derivative which is very difficult to separate from 2CDMAA. Further, the presence of the 2,2-dichloro derivative as an impurity usually interferes with heterocyclic ring formation in the known utilization of the 2CDMAA, for example, its effect in the reaction of 2CDMAA with ammonium acetate to produce 2,4-dimethyl-5-carboethoxyoxazole, a vitamin B6 intermediate, is to lower yield in addition to contaminating the product.

In the present process, the 1,3-diketo precursor of the formula $$CH_3\overset{O}{\overset{\|}{C}}-CH_2-\overset{O}{\overset{\|}{C}}-Q$$

in solution in an alcohol solvent, is nebulized in a nebulizing chlorinator such as described in U.S. Pat. No. 4,468,356, the disclosure of which is incorporated herein by reference, but not limited thereto, by or in the presence of chlorine gas or a mixture of chlorine gas and inert gas such as nitrogen, wherein chlorination of the nebulized precursor takes place rapidly at relatively high temperatures in a chlorination zone. The product is recovered in substantially pure form by stripping the alcohol solvent.

The present process enables the economical production of the desired 2-chloro-1,3-diketo compounds in substantially pure form, in high yield without substantial attendant by-product formation and the resultant need for costly purification procedures and apparatus. In this process a very short residence time within a chlorination zone (defined below), for example, less than about one second for the apparatus shown in the aforesaid patent at relatively high temperatures with very intimate mixing of the reactants in select alcoholic solvents is employed and avoids the formation of a useless mixture of chlorination products.

The chlorination zone is the space intermediate the nebulizing means outlet (tip 20 of said patent) and the reactor walls, in which space the chlorination reaction takes place. It is noted that in said patent, the nebulizing action of the chlorination medium (Cl2 or a mixture of Cl2 and N2) takes place initially approximately at the nebulizer tip outlet. In other forms of nebulizing chlorinators, however, the initial nebulizing action may take place at a point somewhat removed from the points of emission of the precursor solution and the chlorination medium into the reactor. Such would occur, for example, where the precursor solution and the chlorination medium entered the reactor at different locations but were directed and under sufficient pressure to impinge on each other to effect the nebulization. In all such systems, however, the contacting of the precursor solution and the chlorination medium occurs "in said nebulizing means" in accordance with the present invention.

Although the configuration of the nebulizer may be widely varied, the concentric relationship of the chlorination medium feed conduit and the diketo reactant solution feed conduit shown in the aforementioned patent are highly preferred in that it tends to maximize the amount of reactant material which may be provided to the reaction zone.

The invention is defined as the process for preparing a 2-chloro-1,3-diketo compound of the formula $$CH_3\overset{O}{\overset{\|}{C}}-\overset{Cl}{\overset{|}{CH}}-\overset{O}{\overset{\|}{C}}-Q$$

wherein Q is an amino, substituted amino, or a hydrocarbyloxy group, in a nebulizing chlorinator having wall means enclosing a chlorination zone, means for cooling said wall means, and nebulizing means communicating with said zone, said process comprising (a) feeding a solution of the unchlorinated 1,3-diketo precursor of said compound in an alcohol solvent to said nebulizing means, (b) contacting said solution in said nebulizing means with a stream of gaseous chlorination medium to nebulize said solution into said zone and to effect rapid chlorination of said precursor, wherein the molar ratio of Cl2/precursor feeds to the chlorinator is from about 0.7 to about 1.4, and wherein the temperature of said zone is from about 60° C. to about 210° C., and (c) collecting the chlorinated product from the cooled wall means of said chlorinator.

In the process, the precursor solution is preferably fed at a temperature of from about 10° to about 30° C. under suitable pressure, e.g. from about 5-15 psig for a small nebulizer tip outlet of about 2.0 mm², and up to about 60 psig or higher for a large outlet of about 100 mm² which may be employed in commercial scale operations. It is preferred to collect the chlorinated product from the walls of the reactor which are maintained at from about 20° C. to about −10° C.

In the process, the solvated 1,3-diketo reactant can be nebulized with chlorine gas alone, but the preferred method is to use a sufficient volume of chlorination medium to ensure a finely divided reactant spray mixture, and for this reason the chlorination medium pressure preferably is increased with an inert diluent such as N2. The useful pressures for this medium can range widely, the lower for laboratory size apparatus, and of course the higher for larger, commercial scale apparatus.

In more general embodiments of the present invention the molar feed ratios to the nebulizer of Cl2/N2 range from about 10 to about 0.2, and of Cl₂/precursor from about 0.7 to about 1.4, the feed pressures for each of Cl₂ and N₂ range from about 1 to about 30 psig and for precursor solution from about 0 to about 30 psig, the feed temperatures for each of Cl₂, N₂ and precursor solution range from about 0° C. to about 30° C., and the concentration of precursor in the solvent ranges from about 15% to about 70% by weight of the solution.

In more specific embodiments of the invention the molar feed ratios to the nebulizer of Cl₂/N₂ range from about 5 to about 0.5, and of Cl₂/precursor from about 0.83 to about 1.2, the feed pressures for each of Cl₂ and N₂ range from about 5 to about 20 psig and for precursor solution from about 0 to about 20 psig, the feed temperatures for each of Cl₂, N₂ and precursor solution range from about 10° C. to about 25° C., and the concentration of precursor in the solvent ranges from about 15% to about 50% by weight of the solution.

In this process, the concentrations of the diketo reactants (precursors) in the solvents are carefully controlled to prevent over and under chlorination. The desired monochlorinated product is recovered by stripping the volatile solvent at reduced pressure, and therefore, the preferred alcohol solvents include methanol, ethanol, and n-propanol with methanol being most preferred since the stripping step is best facilitated therewith. Useful solvents in general are alcohols of 1-20 carbons, and preferably straight chain of 1-10 carbons. For the precursor N,N-dimethylacetoacetamide (DMAA), it is desirable to have the higher solution concentrations in order to minimize the stripping operation. However, at concentrations over about 70%, overchlorination occurs, attended by lowered yield and the need for complicated and expensive product purification. The molar feed ratio of Cl₂/DMAA is most preferably in the range of from about 0.9 to about 1.1. At higher ratios, overchlorination usually occurs.

It is known in the art of chlorination that alcohols react with gaseous chlorine at elevated temperatures and high chlorine gas concentrations and that such reactions often generate a hazard known as "chlorine fire." Therefore, in order to keep the ratio of alcohol to chlorine high, the reaction mixture may be diluted with an inert co-solvent which is compatible with the alcohol and the diketo reactant. It is desirable that the co-solvent also be a low boiling compound capable of being completely stripped at reduced pressure. Such co-solvents include acetic acid, propionic acid, formic acid, butyric acid and the like.

The invention may utilize all primary alcohol solvents which are liquids at room temperature and the method of product recovery desired governs to a large extent the alcohol selected as solvent. For example, if the product is recovered by stripping, then low boiling alcohols are preferred and most preferred are those of 1-3 carbon atoms. However, the product can be recovered by filtration if the solvent alcohol can be solidified at convenient temperatures. For example, hendecanol with a melting point of 19° C. could be used as the solvent and the liquid product recovered by cooling the solution below the solvent melting point and filtering it away from the product.

Exemplary of the compounds (precursors) that can be chlorinated in the 2-position by this process are: amides of the formula

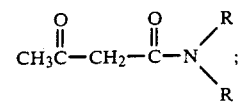

and esters of the formula

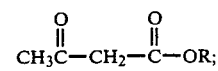

wherein each R substituent is selected from alkyl of 1-20, preferably 1-8 carbons, aryl of 6-10 carbons, preferably phenyl, cycloalkyl of 4-8 carbons, preferably cyclohexyl, or said R substituents substituted (as appropriate, i.e., with a different group) with 1-3 substituents selected from alkyl of 1-4 carbons, alkoxy of 1-4 carbons, halogen, CN, NO₂, alkanoyl of 1-4 carbons, or alkanoyloxy of 1-4 carbons.

EXAMPLES 1-9

N,N-dimethylacetoacetamide (DMAA) in a variety of solvents and concentrations shown in Table I was fed at a measured rate of 0.0154 moles of DMAA/min. at about 20° C. into the inner tube 24 of the nebulizer of the chlorinator shown in the drawing of the aforesaid U.S. Pat. No. 4,468,356 and described therein. The lower esterification unit 12 of the patent plays no part in the present invention. The present DMAA feeds at about 25° C. were nebulized with a gaseous chlorination medium fed at about 20°-25° C. between the outer tube 22 and inner tube 24 at from about 0.1 to about 0.6 CFH (pressure of about 10 psig) and comprising chlorine and nitrogen in a molar ratio of Cl₂/N₂ of about 1/1 metered to the nebulizer at a measured rate approximately stoichiometrically necessary for monochlorination of the DMAA fed at the same time to the nebulizer. The reaction took place in the chlorination zone indicated by dotted lines 30 in said patent at a temperature of from about 70° C. to about 180° C. and the product was condensed on the walls 26 of the reactor which were maintained at a reduced temperature of less than about 20° C., and collected in a nitrogen purge tank (not shown). The effluent gases including nitrogen and HCl were taken off the top of the purge tank and transferred to an HCl scrubber in known manner and eventually vented to the atmosphere. The purged product was stripped on a laboratory rotary evaporator at 70° C. and 35 mm pressure. The residue was assayed by liquid chromatography for 2-chloro-N,N-dimethylacetoacetamide target product, unreacted DMAA, and 2,2-dichloro-N,N-dimethylacetoacetamide by-product. The results of these experiments which evaluated the various solvents are summarized in Table 1 and show that only alcohols are effective as the major solvent component for the present monochlorination.

EXAMPLES 10-14

In Examples 10-14, solvent systems comprising acetic acid containing varying proportions (5% to 50% by weight) of methanol and containing dissolved N,N-dimethylacetoacetamide at 20% concentration were fed to the same apparatus as used in Examples 1-9 and nebulized with nitrogen containing a stoichiometric amount of chlorine for monochlorination wherein the molar ratio of Cl₂/N₂ was again approximately 1/1. The reaction and feed conditions were essentially the same as in Examples 1-9 except as modified for the Table 2 experiments and noted therein. The resulting material was collected as above in a nitrogen purge tank and stripped of residual solvent at 70° C. and 35 mm pressure. The resultant product was analyzed by liquid chromatography and the results of these experiments are summarized in Table 2. As shown in this table, acetic acid is a suitable cosolvent and is most effective in combination with higher concentrations of methanol.

TABLE 1

| Example | Solvent | Feed Wt % DMAA[a] | Feed Cl$_2$/DMAA | Product Analysis, Weight % | | |
|---|---|---|---|---|---|---|
| | | | | DMAA | 2 CDMAA[b] | 2,2 CDMMA[c] |
| 1 | Water | 50 | 0.94 | 40.5 | 51.5 | 0 |
| 2 | Ethylene Glycol | 50 | 0.97 | 27.5 | 22.5 | 0.2 |
| 3 | Formic Acid | 25 | 1.04 | 23.6 | 75.1 | 0 |
| 4 | Acetic Acid | 20 | 0.98 | 4.6 | 87.8 | 6.9 |
| 5 | Methyl Acetate | 25 | 1.06 | 1.3 | 78.4 | 19.5 |
| 6 | Methanol | 40 | 1.05 | 0.7 | 98.6 | 0.6 |
| 7 | Ethanol | 25 | 0.99 | 0.7 | 98.8 | 0.5 |
| 8 | Isopropanol | 20 | 1.01 | 10.0 | 86.6 | 2.2 |
| 9 | n-Propanol | 20 | 0.98 | 2.1 | 96.8 | 0.3 |

[a]N,N-dimethylacetoacetamide
[b]2-Chloro-N,N-dimethylacetoacetamide
[c]2,2-Dichloro-N,N-dimethylacetoacetamide

TABLE 2

| Example | Acetic Acid Wt % Methanol | Feed % DMAA | Feed Cl$_2$/DMAA | Product Analysis, Weight % | | |
|---|---|---|---|---|---|---|
| | | | | DMAA | 2 CDMAA | 2,2 CDMAA |
| 10 | 5.0 | 20 | 0.98 | 3.9 | 90.5 | 5.1 |
| 11 | 10.0 | 20 | 1.03 | 2.8 | 91.6 | 5.2 |
| 12 | 20.0 | 20 | 1.04 | 1.0 | 94.2 | 4.5 |
| 13 | 35.0 | 20 | 1.02 | 1.1 | 96.7 | 2.2 |
| 14 | 50.0 | 20 | 1.00 | 0.6 | 98.2 | 1.2 |

The invention has been described in detail with particular reference to preferred embodiments thereof, but it will be understood that variations and modifications can be effected within the spirit and scope of the invention.

I claim:

1. Process for preparing a 2-chloro-1,3-diketo compound of the formula

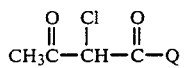

wherein Q is a member selected from the group consisting of:
(i) an amino group,
(ii) a substituted amino group of the formula

wherein each R substituent is selected from the group consisting of alkyl groups of 1-20 carbons, aryl groups of 6-10 carbons, cycloalkyl groups of 4-8 carbons, or said R substituents substituted with 1-3 of alkyl of 1-4 carbons, alkoxy of 1-4 carbons, halogen, CN, NO$_2$, alkanoyl of 1-4 carbons or alkanoyloxy of 1-4 carbons, and
(iii) the group —OR wherein R is a substituent as defined above in (ii),
in a nebulizing chlorinator having wall means enclosing a chlorination zone, means for cooling said wall means, and nebulizing means communicating with said zone, said process comprising
(a) feeding a solution of the unchlorinated 1,3-diketo precursor of said compound selected from N,N-dimethylacetoacetamide, N-methylacetoacetamide, ethylacetoacetate and methylacetoacetate in an alcohol solvent to said nebulizing means,
(b) contacting said solution in said nebulizing means with a stream of gaseous chlorination medium to nebulize said solution into said zone and to effect rapid chlorination of said precursor, wherein the molar ratio of Cl$_2$/precursor feeds to the chlorinator is from about 0.7 to about 1.4, and wherein the temperature of said zone is from about 60° C. to about 210° C., and
(c) collecting the chlorinated product from the cooled wall means of said chlorinator.

2. The process of claim 1 wherein the wall means of said reactor are cooled to about 30° C. to about −10° C.

3. The process of claim 1 wherein the chlorination medium feed pressure is from about 5 to about 20 psig.

4. The process of claim 1 wherein Q is selected from groups of the formula

wherein each R substituent is selected from alkyl of 1-20 carbons, aryl of 6-10 carbons, cycloalkyl of 4-8 carbons, or said R substituents substituted with 1-3 of alkyl of 1-4 carbons, alkoxy of 1-4 carbons, halogen, CN, NO$_2$, alkanoyl of 1-4 carbons or alkanoyloxy of 1-4 carbons.

5. The process of claim 1 wherein Q is —OR wherein R is a substituent selected from alkyl of 1-20 carbons, aryl of 6-10 carbons, cycloalkyl of 4-8 carbons, or said R substituents substituted with 1-3 of alkyl of 1-4 carbons, alkoxy of 1-4 carbons, halogen, CN, NO$_2$, alkanoyl of 1-4 carbons or alkanoyloxy of 1-4 carbons.

6. The process of claim 4 wherein the temperature in said reaction zone is from about 70° C. to about 180° C.

7. The process of claim 6 wherein the alkyl of each said R substituent is from 1-8 carbons.

8. The process of claim 1 wherein the chlorination zone temperature is from about 70° C. to about 180° C., the molar feed ratio of $Cl_2$/precursor is from about 0.83 to about 1.2, the solvent is selected from methanol, ethanol, n-propanol, and mixtures thereof with acetic, propionic, formic or butyric acid wherein said acid comprises less than about 65% by weight of the mixture, and wherein the concentration of precursor in the feed solution is from about 15% to about 50% by weight of the solution.

9. The process of claim 8 wherein said precursor is N,N-dimethylacetoacetamide and the solvent is methanol.

* * * * *